US005976474A

United States Patent [19]
Barnstead

[11] Patent Number: 5,976,474
[45] Date of Patent: Nov. 2, 1999

[54] STERILIZER WITH STERILE DISCHARGE

[76] Inventor: William A. Barnstead, 19 Potter Pond, Lexington, Mass. 02173

[21] Appl. No.: 09/104,805

[22] Filed: Jun. 25, 1998

[51] Int. Cl.[6] .................................................. A61L 2/04

[52] U.S. Cl. .......................... 422/298; 422/292; 422/295; 422/307

[58] Field of Search ................................ 422/26, 28, 33, 422/292, 295, 298, 307

[56] References Cited

U.S. PATENT DOCUMENTS 4,193,818 3/1980 Young et al. ............................ 422/33
4,239,730 12/1980 Fahlvik et al. .......................... 422/295
4,637,916 1/1987 Hennebert et al. .................... 422/295

*Primary Examiner*—Elizabeth McKane
*Assistant Examiner*—Fariborz Moazzam

[57] ABSTRACT

A sterilizing machines for decontaminating articles of dangerous biological material features an arrangement whereby all of the gas discharged from the sterilizer chamber during a sterilization cycle passes through a removable filter situated within the sterilization chamber.

6 Claims, 2 Drawing Sheets

43 15 16 19 20 17 10 14 13 13 44 11 18 12 37 11 14 26 21 28 41 42 34 29 40 35 30 31

STERILIZER WITH STERILE DISCHARGE

BRIEF SUMMARY OF THE INVENTION

This invention relates to sterilizing machines for decontaminating articles of dangerous biological material. It features an arrangement whereby all of the gas discharged from the sterilizer chamber passes through a filter situated within the sterilization chamber.

DETAILED DESCRIPTION

Figure 1:
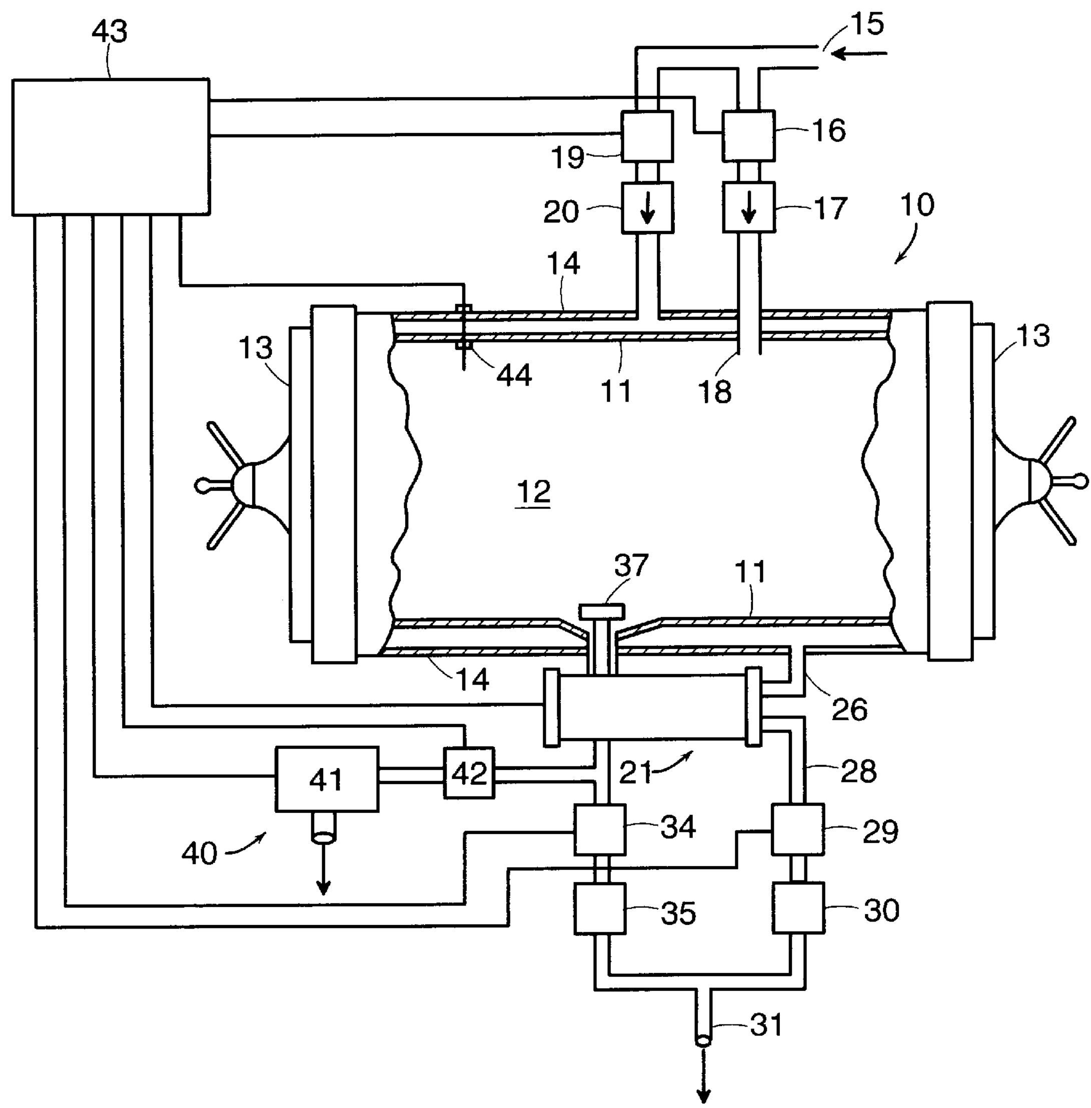
FIG. 1 shows a sterilizer according to the invention.
Figure 2:
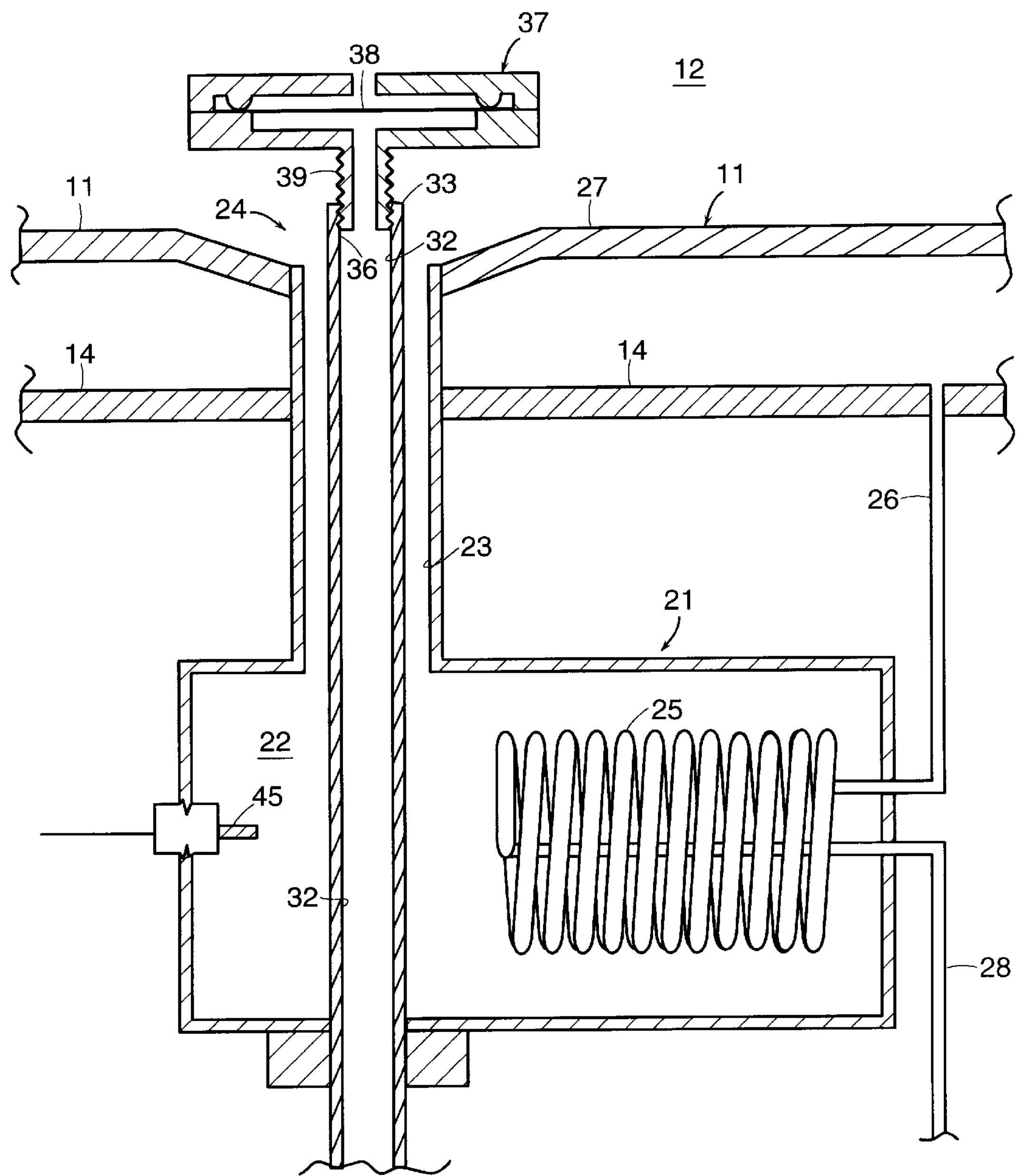
FIG. 2 shows a detail of the serilizer of FIG. 1.

Referring to the Figures, sterilizer 10 according to the invention has interior wall 11 which with closed doors 13 enclose interior space 12 within which articles to be serilized are placed. Jacket wall 14 surrounds interior wall 11 and defines a space around interior wall 11 through which steam can circulate.

Steam source 15 is connected through control valve 16 and check valve 17 to steam inlet port 18 which admits steam into interior space 12. Steam source 15 is also connected through control valve 19 and check valve 20 to the space between interior wall 11 and jacket wall 14.

Condensate collector 21 includes chamber 22 positioned below wall 14. Conduit 23 connects condensate well 24 in the bottom 27 of interior space 12 to chamber 22. Heater 25 inside chamber 22 is connected through conduit 26 to the space between interior wall 11 and jacket wall 14 and through conduit 28 control valve 29 and steam trap 30 to open drain 31. In particular, the only fluid passage connecting to the interior of chamber 22 is conduit 23.

Vent passage 32 has an inner end 33 positioned within interior wall 11. Vent passage 32 passes down the lumen of conduit 23, through condensate collector 21, control valve 34 and trap 35 to outer end 31, which is open to the ambient and drain. Inner end 33 terminates in threaded coupling 36.

Filter holder 37 holds filter 38 and has threaded coupling 39 which mates with coupling 36 and permits the filter holder to be removed from the end of the vent passage.

Evacuation system 40 including vacuum pump 41 and control valve 42 is connected to draw from vent passage 32 from a point downstream from filter holder coupling 36.

Controller 43 includes processors, information storage, operator interface, and input and output facilities to receive instructions from an operator and control the operation of the sterilizer according to a defined program. Controller receives data from temperature sensor 44 positioned within interior space 12 and from temperature sensor 45, positioned within condensate collector chamber 22, and emits signals controlling vacuum pump 41 and valves 16, 19, 42, 34, and 29.

Filter 38 is made of materials suffering no significant damage at sterilization conditions and has a pore size to retain particles of the size of pathogenic microorganisms. In particular, a suitable filter is offered for sale by the Balston division of Watman, Inc. as item number CS-SA.

The operation of the sterilizer is as follows. A filter holder with a clean filter is installed by coupling it to the inner end of the of the vent passage. Articles to be sterilized are placed within the interior space, and the doors of the sterilizer are closed. Valves 16 and 34 are closed. Valve 42 is opened and the vacuum pump is started. The action of the vacuum pump pulls the gases out of the interior space. After the evacuation has been completed, valve 42 is closed and steam is admitted to the interior space through valve 16 and to the jacket through valve 19, and valves 34 and 29 are opened. The steam entering the interior space will displace any residual air remaining in the interior space. In general, the air will be concentrated in the bottom of the interior space and so be discharged through the filter and valve 34 to the ambient. Some of the steam admitted to the interior space will condense on contacting the initially cool articles within and walls of the interior space. This condensate will gather at the bottom of the interior space and drain into the condensate collector. The steam admitted to the jacket will maintain the temperature of the interior space and steam from the jacket passing through the condensate collector will evaporate the condensate drained into the condensate collector back into the interior space. After the desired interval of sterilization is completed the steam supplies are shut off and a door opened to remove the now sterile articles. The filter holder with filter element can be removed for replacement. The removed filter holder and filter have been sterilized because they were within the interior space during the sterilization cycle and can be discarded as uncontaminated waste.

It may be particularly noted, that all of the gases passing out of the interior space pass out through the filter which retains any microorganisms, preventing them from exiting with the gases. The filter, being positioned within the interior space, is sterilized along with the articles. Particles both biological and otherwise are deposited in the filter as a result of the passage of gas through it so that it becomes clogged with use. The filter holder with the filter is therefore advantageously decoupled from the vent passage and discarded after a sterilization cycle. The filter holder and filter have however been themselves sterilized at this point and require no special handling.

I claim:

1. A sterilizer for killing living organisms in goods comprising a wall enclosing an interior space and having one or more doors which when open give access to said interior space, and when closed complete the enclosure of said interior space, a steam inlet port connected into said wall for admitting steam into said interior space, said steam inlet port being connected through a control valve to a source of steam, a vent passage having a first end opening into said interior space and a second end opening to the ambient, said first end of said vent passage terminating in a filter holder coupling, a filter holder holding a filter having a pore size to retain particles of the size of biological microorganisms, said filter holder having a mating coupling mating with said filter holder coupling, and being removably attached through said mating coupling and said filter holder coupling to said first end of said vent passage so that fluid can enter said vent passage from said interior space only through said filter holder and said filter held therein, all passages through said wall communicating with said interior space being constructed and arranged so that when said doors are closed material can exit from said interior space to the ambient only through said filter holder.

2. A sterilizer as claimed in claim 1, including a condensate collector with a chamber and a heater for evaporating material within said chamber, said chamber being connected to receive condensate draining from the bottom of said interior space and discharge evaporate from the evaporation thereof back into said interior space.

3. A sterilizer as claimed in claim 1, including an evacuation system for evacuating gas from said interior space, said evacuation system being connected to draw gas from said vent passage at a point downstream from said filter holder coupling.

4. A sterilizer as claimed in claim 1, wherein said filter holder is positioned near the bottom of said interior space.

5. A sterilizer as claimed in claim 1, including a collector positioned to collect condensate from said interior space and a heater positioned to re-evaporate such condensate into said interior space.

6. A sterilizer for killing living organisms in goods comprising a wall enclosing an interior space and having one or more doors which when open give access to said interior space, and when closed complete the enclosure of said interior space, a steam inlet port connected into said wall for admitting steam into said interior space, said steam inlet port being connected through a control valve to a source of steam, a vent passage having a first end opening into said interior space and a second end opening to the ambient, a condensate collector for re-evaporating condensate, said condensate collector including a chamber and a heater, said chamber being positioned below said interior space, said condensate collector being connected to receive liquid condensate draining from said interior space and to discharge revaporized condensate into said interior space, wherein said vent passage passes through said chamber without having fluid connection thereto.

* * * * *